United States Patent
Okanojo et al.

(10) Patent No.: US 10,481,098 B2
(45) Date of Patent: Nov. 19, 2019

(54) LUMINOMETER APPARATUS

(71) Applicant: Hitachi, Ltd., Tokyo (JP)

(72) Inventors: Masahiro Okanojo, Tokyo (JP);
Hideyuki Noda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 101 days.

(21) Appl. No.: 15/547,910

(22) PCT Filed: Apr. 30, 2015

(86) PCT No.: PCT/JP2015/062976
§ 371 (c)(1),
(2) Date: Aug. 1, 2017

(87) PCT Pub. No.: WO2016/174766
PCT Pub. Date: Nov. 3, 2016

(65) Prior Publication Data
US 2018/0024070 A1 Jan. 25, 2018

(51) Int. Cl.
*G01N 21/76* (2006.01)
*G01N 35/02* (2006.01)
(Continued)

(52) U.S. Cl.
CPC ............... *G01N 21/76* (2013.01); *C12Q 1/02* (2013.01); *G01N 35/00871* (2013.01);
(Continued)

(58) Field of Classification Search
CPC ........ C12Q 1/02; G01N 21/76; G01N 21/763; G01N 35/04; G01N 35/025;
(Continued)

(56) References Cited

U.S. PATENT DOCUMENTS 6,691,748 B1 * 2/2004 Tajima .................... B01L 9/543
141/130

FOREIGN PATENT DOCUMENTS

| JP | H06-174730 A | 6/1994 |
| JP | 2008-096324 A | 4/2008 |
| JP | 2011-153946 A | 8/2011 |

OTHER PUBLICATIONS

Hattori, N., et al., Enhanced Microbial Biomass Assay Using Mutant Luciferase Resistant to Benzalkonium Chloride, Analytical Biochemistry, 2003, 319, pp. 287-295.

* cited by examiner

*Primary Examiner* — Liban M Hassan
(74) *Attorney, Agent, or Firm* — Procopio, Cory, Hargreaves & Savitch LLP

(57) ABSTRACT

A luminometer apparatus includes, inside a light-shielded room, a container rack loaded with holding containers, a dispensation mechanism that dispenses a liquid, a rotary plate that turns, while holding a plurality of reaction containers which accommodate a mixture liquid of a sample and a luminescent reagent on a concentric annular plate, and is provided with a gap allowing the container rack to pass therethrough between at least a pair of adjacent ones of the reaction containers, and a photodetection unit that performs luminescence measurements. The light-shielded room has an insertion opening having a width allowing for insertion of the container rack and provided to be openable and closable. The rotary plate is provided with a region in which the container rack can be installed inside a region of passage of the reaction containers, when turning, and is provided to be turnable where the light-shielded room is in a closed state.

13 Claims, 12 Drawing Sheets

(51) Int. Cl.
*G01N 35/04* (2006.01)
*C12Q 1/02* (2006.01)
*G01N 35/00* (2006.01)
*G01N 35/10* (2006.01)

(52) U.S. Cl.
CPC ........... G01N 35/025 (2013.01); G01N 35/04 (2013.01); G01N 35/1004 (2013.01); G01N 35/1009 (2013.01); *G01N 2035/00277* (2013.01); *G01N 2035/00306* (2013.01); *G01N 2035/00356* (2013.01); *G01N 2035/0444* (2013.01); *G01N 2201/0231* (2013.01); *G01N 2201/064* (2013.01)

(58) Field of Classification Search
CPC ........... G01N 35/1004; G01N 35/1009; G01N 35/00871; G01N 2201/064; G01N 2201/0231; G01N 2035/0422; G01N 2035/0432; G01N 2035/00306; G01N 2035/00277; G01N 2035/00356; G01N 2035/0444
USPC ...................................... 435/287.3
See application file for complete search history.

LUMINOMETER APPARATUS

CROSS-REFERENCE TO RELATED APPLICATIONS

This application is a U.S. National Stage entry of PCT Application No. PCT/JP2015/062976, filed on Apr. 30, 2015, the contents of which are incorporated herein by reference.

TECHNICAL FIELD

The present invention relates to a luminometer apparatus that detects presence of a cell or measures the number of cells included in a sample by luminescence measurement.

BACKGROUND ART

For management of a microbiological quality of raw materials, intermediates, and final products of drugs and medicines, the manufacturers of medicinal chemicals are obligated to measure the number of cells of microbes (bacteria and true fungi) included in them according to the Standards of Japanese Pharmacopoeia (JP) prescribed by the Ministry of Health, Labour and Welfare in Japan.

As a method for cell number measurement, a culture method is generally adopted in which the number of colonies (Colony Forming Units: CFUs) formed through cultivation for a certain period is visually measured. Because about one week is required as the cultivation period, waiting for results of cell number measurements by a quality management department is entailed in each of the following phases: raw material reception, intermediate production, and final product shipment. This has imposed inordinate economic burdens on the manufacturers.

As a measurement method that is faster than a culture method, An ATP (Adenosine TriPhosphate) luminometric assay is known.

The ATP luminometric assay is a method that measures luminescence generated by reacting ATP extracted from within microbes living in a sample with a luminescent reagent by a photodetection unit such as a photomultiplier tube and estimates the number of living cells from a quantity of luminescence thus measured (refer to Nonpatent Literature 1). A sample container is placed close to a photodetection unit and measurement is performed. Hence, luminescence derived from a single discrete container may sometimes be detected, which was not detected by a commonly used luminometer apparatus whose structure and sensitivity are not enough to detect it.

In an analysis method by luminometric detection, after preserving sample containers under a light shielding environment, it has heretofore been practiced to repeat a process of measuring a background noise which is luminescence derived from sample containers and selecting sample containers making a low background noise (Refer to, e.g., Patent Literature 1).

Besides, a quantity of ATP per bacterium is extremely small as compared with a quantity of ATP included in a large cell of a true fungus, human, etc. Hence, when a microbial contamination or ATP contamination occurs with incursion of a substance derived from a worker or an external environment into the luminometer apparatus, a quantity of ATP derived from bacteria is over-estimated.

To prevent a microbial contamination or ATP contamination, it is known that it is advisable to carry out a process including pretreatment of microbes and luminescence measurement, enveloped by a clean space such as a safety cabinet. To enhance the accuracy in measuring a quantity of ATP derived from bacteria, it is required to confine a space where the luminometer apparatus is used within such a clean space. Taking practical working operability into account, it is required to downsize the luminometer apparatus that is able to automatically carry out every process without intervention of a worker in any process, so that the apparatus can be installed inside a safety cabinet.

For example, Patent Literature 2 describes an automatic chemical analysis apparatus in which a reagent holder is installed inside a reaction disk having a plurality of reaction tubes installed therein. Also, Patent Literature 3 discloses an analysis apparatus equipped with a reagent disk, a member holding a sample dispensation chip and a reaction container, and a mechanism carrying the sample dispensation chip and the reaction container.

CITATION LIST

Patent Literature

Patent Literature 1: Japanese Unexamined Patent Application Publication No. 2008-96324
Patent Literature 2: Japanese Unexamined Patent Application Publication No. Hei 6-174730
Patent Literature 3: Japanese Unexamined Patent Application Publication No. 2011-153946

Nonpatent Literature

Nonpatent Literature 1: Analytical Biochemistry, vol. 319, pp. 287-295, 2003

SUMMARY OF INVENTION

Technical Problem

Even in an instance where containers making a low background noise were selected beforehand and luminescence measurement was performed using them as sample containers, as described in Patent Literature 1, it was observed that a background noise derived from a sample container is detected again during luminometric detection. Each time a background noise is detected, it is necessary to replace or discard a sample and a reagent in containers, which makes the measurement time longer and the measurement work cumbersome and might cause an environmental contamination.

Besides, in the analysis apparatus described in Patent Literature 2, for instance, when loading reagent bottles into the reagent holder, a course in which a worker's hand moves overlaps the reaction disk and a contamination from a worker might arise. Moreover, in this apparatus structure, because a course in which a worker's hand moves to load reagent bottles into the reagent holder occurs, there is a need for providing an open side for loading the reagent bottles and a light shielding environment might not be maintained sufficiently. Meanwhile, the apparatus described in Patent Literature 3 has a structure in which a course in which a worker's hand moves hardly overlaps the reagent disk or the like, but the apparatus has a wide breadth and its overall size is liable to enlarge.

And now, if a motor for air-conditioning is directly installed on a luminometer apparatus, a noise is liable to arise in measurement results, affected by vibration of the motor. Meanwhile, if a clean space maintaining portion including the motor for air-conditioning or the like is installed to separate from the luminometer apparatus with an intention to maintain a clean condition entirely in a room, power consumption increases significantly. Therefore, to perform luminescence measurement at a high sensitivity, it is an important challenge to strike a balance between maintaining a light shielding environment and maintaining a clean space.

The present invention is intended to provide a luminometer apparatus having excellent light shielding performance, reducing incursion of contaminants from an external environment or a worker, and capable of measuring a cell under measurement at a high sensitivity.

Solution to Problem

As a preferred embodiment of the present invention, the invention resides in a luminometer apparatus including: inside a light-shielded room shielded from external light, a container rack that is loaded with holding containers, each discretely accommodating at least one selected from a sample and a luminescent reagent which produces a luminescent reaction when mixed with the sample; a dispensation mechanism that dispenses liquid; a rotary plate that turns, while holding a plurality of reaction containers which accommodate a mixture liquid of the sample and the luminescent reagent on a concentric annular plate, and is provided with a gap allowing the container rack to pass therethrough between at least a pair of adjacent ones of the reaction containers; and a photodetection unit that is provided such that it can face through an opening of the rotary plate the bottom of a reaction container which is positioned above the opening and performs luminescence measurements in a state where the light-shielded room is closed. The luminometer apparatus is characterized in that the light-shielded room has an insertion opening having a width allowing for insertion of the container rack and provided to be openable and closable and the rotary plate is provided with a region in which the container rack can be installed inside a region of passage of the reaction containers, when turning, and is provided to be turnable in a state where the light-shielded room is closed.

Advantageous Effects of Invention

According to the present invention, it is possible to realize a luminometer apparatus having excellent light shielding performance, reducing incursion of contaminants from an external environment or a worker, and capable of measuring a cell under measurement at a high sensitivity.

DESCRIPTION OF EMBODIMENTS

Figure 1:
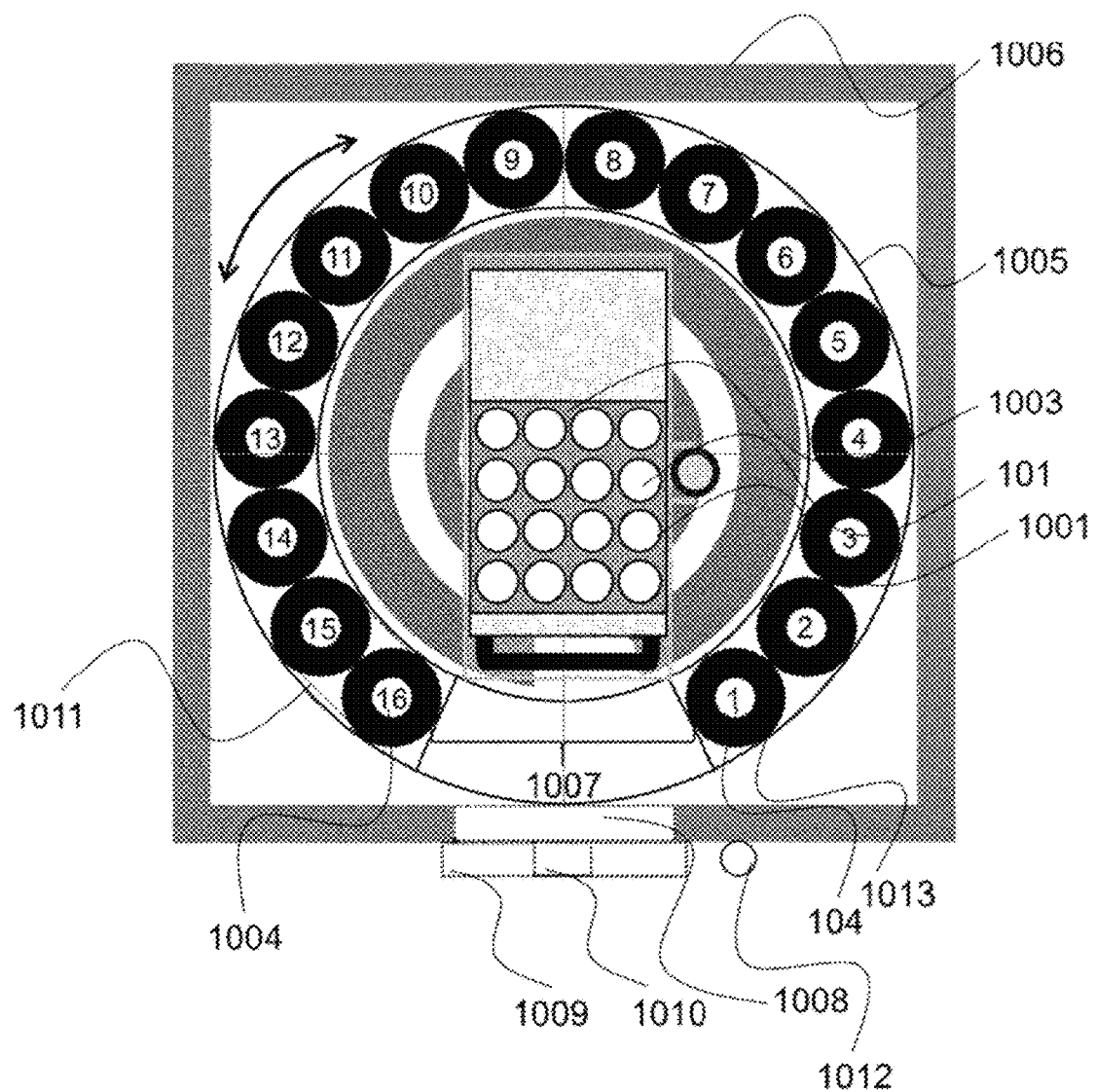
FIG. 1 is a diagram depicting a part of a luminometer apparatus pertaining to an embodiment when viewed from above.

In the following, embodiments of the present invention will be described with the aid of the drawings.

In the following description, a luminometer apparatus of an embodiment is described, taking an instance where it is applied to an ATP luminometric assay as an example.

ATP to be detected by an ATP luminometric assay is an organic compound acting as a source of energy for life activity and existing in a cell of every living organism.

An ATP luminometric assay generally includes decomposing ATP derived from dead microbes in a sample by an enzyme, extracting ATP from within living microbes using a surfactant or the like, and causing a luminescent reaction of the extracted ATP with a luminescent reagent such as, e.g., luciferase luciferin. Thus obtained luminescence is measured by a photodetector such as a photomultiplier tube and the number of living cells included in the sample is estimated from a quantity of luminescence (refer to Nonpatent Literature 1).

A quantity of ATP in a microbe depends on cell size and a quantity of ATP in a bacterium having a small cell size is approximately $1.5 \times 10^{-18}$ mol ATP/CFU (0.001 fmol/CFU=1 amol/CFU) (refer to Nonpantent Literature 1).

Detection sensitivity of an ATP luminometric assay which is commonly used currently ranges from $1 \times 10^{-15}$ to $1 \times 10^{-16}$ mol ATP (1 to 0.1 fmol) and this is not enough to reach a detection sensitivity to detect ATP in one bacterium, only enough for approximately 100 to 1000 bacteria.

Hence, in the present state, it is generally impossible for an ATP luminometric assay to observe the number and presence of 1 to 100 microbes. However, the present inventors have developed a luminometer apparatus that has high sensitivity and is capable of detecting $1 \times 10^{-18}$ mol ATP, comparable to a quantity of ATP in one bacterium, which is beyond the limit of detection sensitivity by a current ATP luminometric assay. In the process of developing that apparatus, the inventors observed a luminescent phenomenon that has so far treated as an error and has not been reflected in a luminescence measurement result.

With this matter, as a result of further examination made by the present inventors, the inventors found that whether or not a background noise derived from sample containers is generated depends on how frequent and how long the door of the luminometer apparatus is opened and closed under a measurement environment and time it takes to pour samples and reagents into sample containers.

That is, it was observed that, even though sample containers for which no background noise is detected are selected and installed in the luminometer apparatus, after the installation in the apparatus, when light comes in the apparatus from a measurement environment, as the door is opened, the sample containers absorb this light and emit light again, which generates a background noise.

Especially, when measuring many kinds of and a large number of samples, the door has to be opened and closed many times as many as the number of samples under measurement until now. Also, with an increase in the number of samples to be installed in the apparatus, accordingly, the opening space of the door for installing them tends to increase. To reduce a background noise, it is required to reduce the number of times the door is opened and closed for setting and discarding a sample container to a minimum and make the opening space of the door as small as possible.

Figure 2:
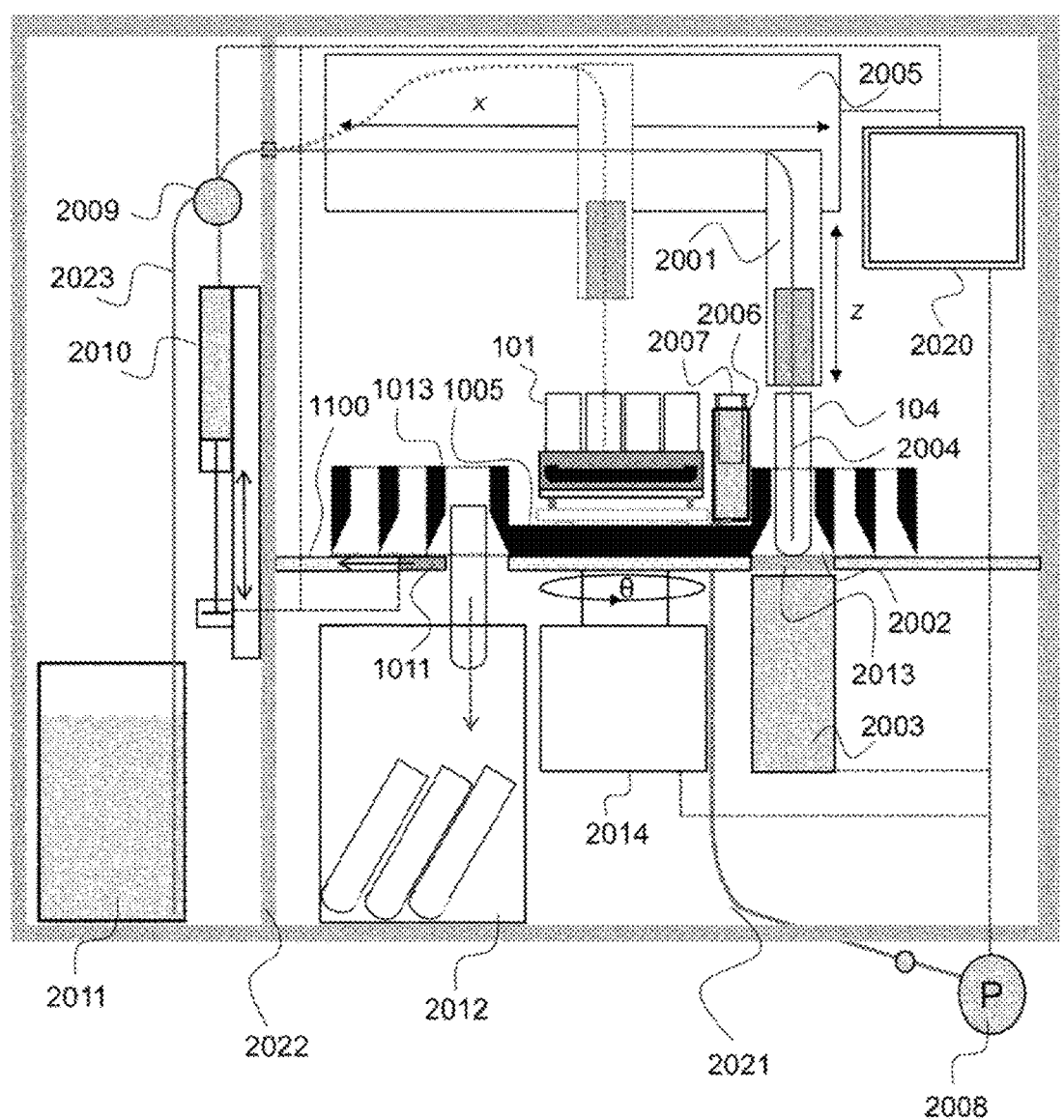
FIG. 2 is a schematic diagram for explaining an internal structure of the luminometer apparatus.

FIG. 1 is a diagram depicting a part of a luminometer apparatus pertaining to an embodiment when viewed from above. FIG. 2 is a schematic diagram for explaining an internal structure of the luminometer apparatus.

And now, in the following description, a "sample" is a liquid substance including a microbe such as a bacterium or true fungus which is subjected to inspection and a "reagent" encompasses a luminescent reagent which emits light by reacting with ATP included in a microbe mentioned above, an ATP extraction reagent which decomposes a cell and extracts ATP, an ATP erasure reagent which decomposes ATP existing in a non-living cell, and a reagent which increases ATP included within a cell.

As depicted in FIG. 1, the luminometer apparatus is provided with a rotary plate 1005 and a container rack 1003 installed in a central region of the rotary plate 1005 inside a light-shielded room 1006.

The container rack 1003 is provided with holding container installation portions 1001, each for installing a holding container 101 which holds at least one selected from a sample and a luminescent reagent.

Also, along an outer circumference of the rotary plate 1005, the rotary plate 1005 is provided with a total of 16 reaction container installation portions 1004 (No. 1 to No. 16) for installing reaction containers 104 (No. 1 to No. 16) to surround the region where the container rack 1003 is installed. At the bottom of each reaction container installation portion 1004 (No. 1 to No. 16), an opening 2002 is provided respectively (see FIG. 2), and each reaction container installation portion 1004 (No. 1 to No. 16) is provided with a light collecting mirror 1013 to surround its outer circumstance (see FIG. 2).

The reaction containers 104 (No. 1 to No. 16) are to accommodate a mixture liquid of at least one of a sample and a luminescent reagent and the other of them which are dispensed from a holding container 101. Between a reaction container installation portion 1004 No. 1 and a reaction container installation portion 1004 No. 16 which are adjacent to each other, a gap 1007 is provided which is slightly broader than the width of the container rack 1003.

The container rack 1003 is provided integral with slides 4001 which slide on rails 4002 provided on a supporting pedestal 4003, as depicted in FIG. 2. The container rack 1003 is so provided as to be pulled out from the light-shielded room 1006 through the gap 1007 between a reaction container 104 No. 1 and a reaction container 104 No. 16 and through an insertion opening 1008 by sliding the slides 4001 on the rails 4002 and to be re-installed in the region inside the reaction container installation portions 1004 (No. 1 to No. 16) by sliding the slides 4001 toward the rotary plate 1005.

By the insertion opening 1008 provided in the light-shielded room 1006, a door 1009 for closing the insertion opening 1008 is provided to be openable and closable. The door 1009 is provided such that it can close the entire insertion opening 1008 and a small door 1010 which is narrower than the door 1009 is further provided to be openable and closable in a central region of the door 1009.

As depicted in FIG. 2, inside the light-shielded room 1006, a dispensation mechanism 2001 having a function of dispensing liquid is provided above the rotary plate 1005.

The dispensation mechanism 2001 includes a nozzle 2004 which takes up and pours out a liquid and an arm 2005 which moves the nozzle 2004 in an arrow x direction in FIG. 2 (a horizontal direction in FIG. 2) or an arrow z direction (a vertical direction in FIG. 2).

The dispensation mechanism 2001 is configured such that motion of the arm 2005 is controlled by a control unit 2020. When a sample or reagent in a holding container 101 is dispensed into a reaction container 104, first, the arm 2005 is driven in the arrow x direction by the control unit 2020 to move the tip of the nozzle 2004 to above the holding container 101. After that, the arm 2005 is driven in the arrow z direction so that the tip of the nozzle 2004 will be inserted into the holding container 101 to take up a sample or reagent in the holding container 101. Then, the arm 2005 is driven in the arrow x direction by the control unit 2020 to move the nozzle 2004 to above the reaction container 104. After that, the arm 2005 is driven in the arrow z direction so that the tip of the nozzle 2004 will be inserted into the reaction container 104 to pour out the sample or reagent taken up into the nozzle 2004. Meanwhile, the control unit 2020 is configured to be operable appropriately by a controller, which is not depicted, provided outside the light-shielded room 1006.

Under the rotary plate 1005, a rotary plate supporting plate 1100 is installed. The rotary plate supporting plate 1100 is hanged onto the supporting pedestal 4003 with a strut 4004 provided to penetrate the rotary plate 1005 through a strut avoidance opening 4005. Under the central region of the rotary plate 1005 (under the supporting pedestal 4003), a rotary plate turning unit 2014 is provided to penetrate the rotary plate supporting plate 1100.

The rotary plate turning unit 2014 is configured such that its turning can be controlled by the control unit 2020 and the rotary plate 1005 turns with the turning of the rotary plate turning unit 2014.

As depicted in FIG. 1, a rotary dial 1012 is provided on the outside of the light-shielded room 1006. The rotary plate turning unit 2014 and the rotary plate 1005 are configured such that they can also be driven to turn by operating the rotary dial 1012.

Under the rotary plate supporting plate 1100, a photodetection unit 2003 which performs luminescence measurements is provided. The photodetection unit 2003 is provided such that, through an opening 2002 provided at the bottom of each reaction container installation portion 1004 (No. 1 to No. 16) of the rotary plate 1005, it can face the bottom of a reaction container 104 which is positioned above the opening 2002, and is configured such that its luminescence measurement operation can be controlled by the control unit 2020.

Although a material of which the rotary plate supporting plate 1100 is made is non-limiting specifically, such a region of the rotary plate supporting plate 1100 that faces the photodetection unit 2003 is made of a photodetection unit protecting material 2013 having light permeability.

The rotary plate supporting plate 1100 is provided with a shutter 1011 configured such that its opening and closing can be controlled by the control unit 2020. Under the shutter 1011, a reaction disposal box 2012 is provided to receive a reaction container 104 dropping through an opening 2002 of the rotary plate 1005, when the shutter 1011 is opened.

Figure 6:
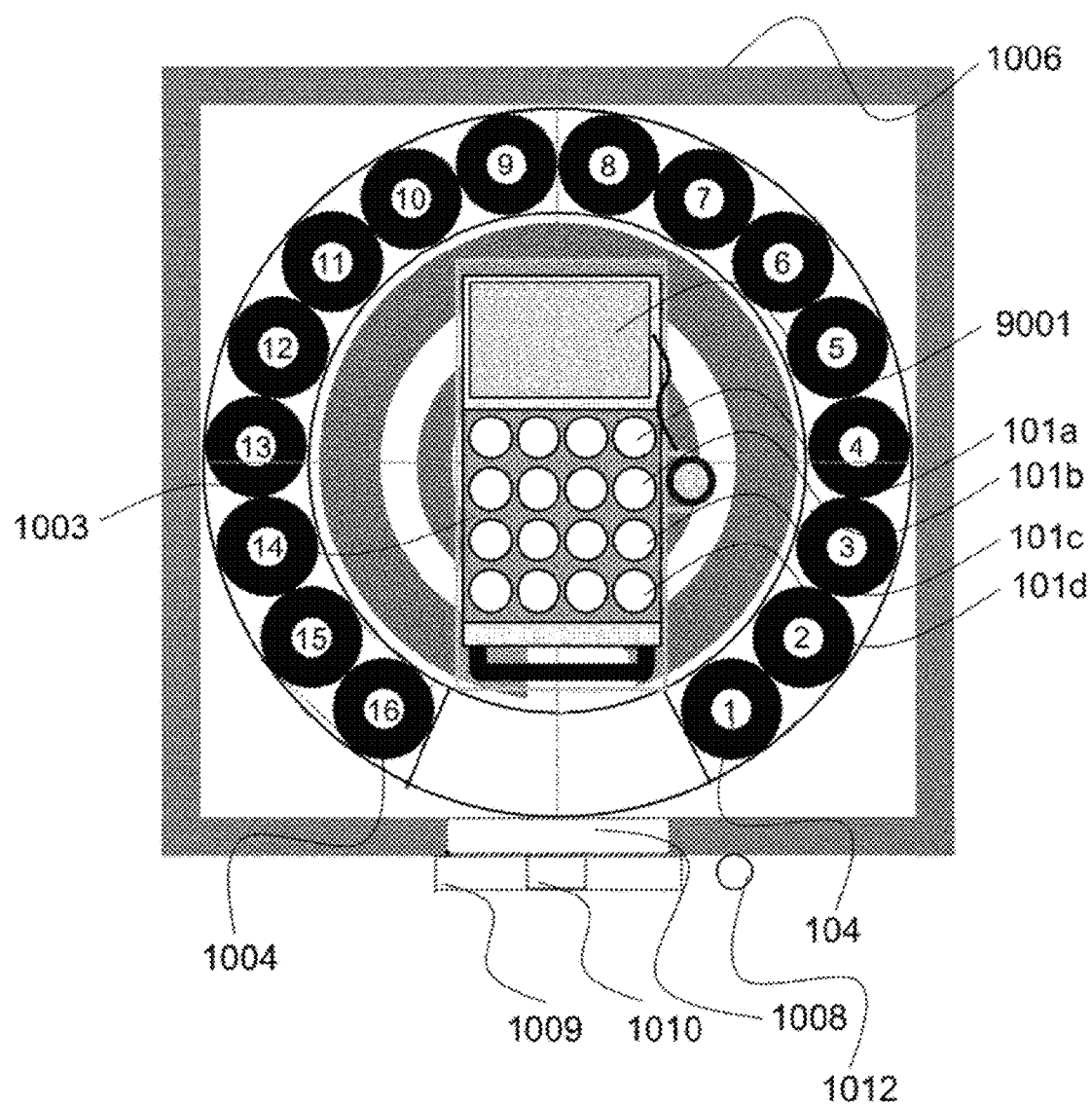
FIG. 6 is a diagram depicting a structure of the luminometer apparatus in which a thermostatic unit is provided close to the container rack.

Upon the slides 4001, a thermostatic unit 9001 which heats the holding containers 101 to keep them in a constant temperature condition is provided adjacent to the container rack 10003, for example, as depicted in FIG. 6. Although the thermostatic unit 9001 is provided adjacent to the container rack 1003 in FIG. 6, thermostatic units 9001 may be installed on lateral sides of the slides 4001.

Figure 7:
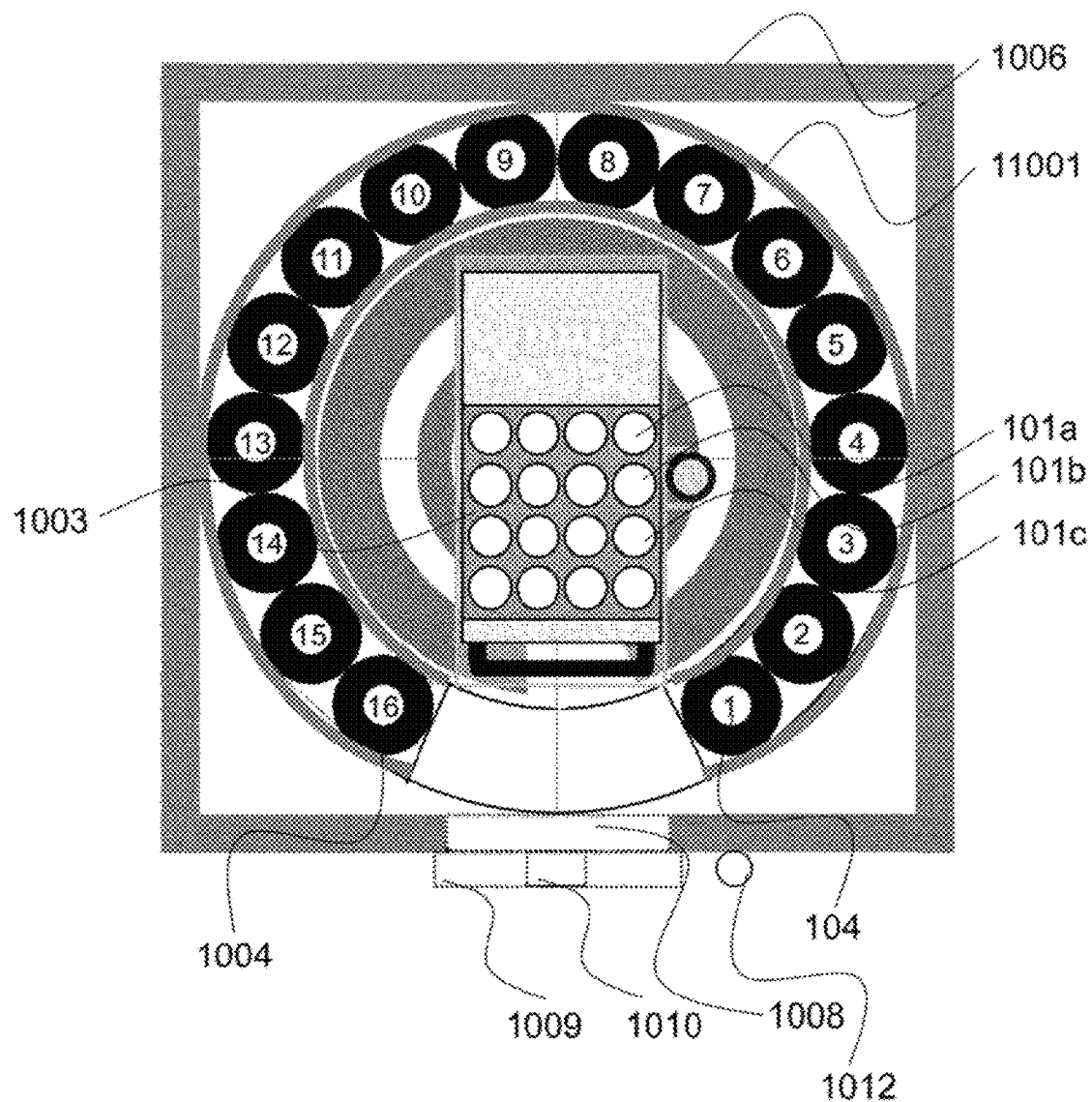
FIG. 7 is a diagram depicting a structure of the luminometer apparatus in which a rotary plate is provided with a thermostatic unit.

Besides, on the periphery of the rotary plate 1005, i.e., the reaction container installation portions 1004, a thermostatic unit 11001 can also be provided which heats the reaction containers 104 suitably to keep them in a constant temperature condition, for example, as depicted in FIG. 7.

Meanwhile, although the thermostatic unit 9001 and the thermostatic unit 11001 are not depicted in FIG. 2, the thermostatic unit 9001 and the thermostatic unit 11001 can also be configured such that their heating operation can be controlled by the control unit 2020, as is the case for the above-mentioned photodetection unit 2003 and others.

Inside the light-shielded room 1006, a cylindrical body 2006 is provided and, inside the cylindrical body 2006, a bottomed filter 2007 is provided to fit in with the inner wall of the cylindrical body 2006.

The cylindrical body 2006 is connected by a tube 2021 with a suction unit 2008 provided outside the light-shielded room 1006 and configure such that its suction operation can be controlled by the control unit 2020.

Although a type of the filter 2007 is non-limiting specifically, filter coarseness should be selected and used appropriately according to the type of a liquid which is fed into the cylindrical body 2006, so that the liquid fed into the cylindrical body 2006 will accumulate in the filter 2007 when it is not sucked in by the suction unit 2008 and the liquid fed into the cylindrical body 2006 will move through the filter 2007 and can be ejected out of the light-shielded room 1006 when it is sucked in by the suction unit 2008.

Inside the light-shielded room 1006, a cleaning solution tank 2011 holding a cleaning solution is installed in a space which is adjacent to the rotary plate 1005 and separated by a partition wall 2022. A suction tube 2023 installed in the cleaning solution tank 2011 is connected to the nozzle 2004 via a three-way valve 2009 and a syringe 2010 is further connected to the three-way valve 2009. The three-way valve 2009 is configured such that its switching action can be controlled by the control unit 2020 and the syringe 2010 is configured such that its actions of delivering and withdrawing a solution can be controlled by the control unit 2020.

According to the luminometer apparatus of the present embodiment, turning of the rotary plate 1005, moving of the nozzle 2004, and luminescence measurement operation of the photodetection unit 2003 can be carried out, while the insertion opening 1008 of the light-shielded room 1006 remains closed; therefore, it is possible to reduce the number of times the insertion opening 1008 is opened and closed. Consequently, the number of times and the amount of stray light incursion form the measurement environment are reduced and luminescence derived from sample containers (background noise) can be prevented. Besides, because operations requiring a worker's hand to enter the light-shielded room 1006 are reduced, contamination from a worker is prevented and it is enabled to perform high-sensitivity luminescence measurements of a substance derived from a cell under measurement in a sample. Also, because the apparatus as a whole is easy to downsize, light shielding management and cleanliness management are easy to perform and high-sensitivity luminescence measurements with incursion of light and a contaminant being suppressed become possible.

Besides, for the luminometer apparatus of the present embodiment, its door 1009 is provided with the small door 1010 which is narrower than the door 1009. Hence, after inserting the container rack 1003 into the light-shielded room 1006 through the insertion opening 1008 and closing the door 1009, it is possible to install the reaction containers 104 inside the light-shielded room 1006 through the small door 1010. Consequently, it is possible to reduce the number of times the door 1009 and the small door 1010 are opened and closed and the opening space of the insertion opening 1008 to a requisite minimum and incursion of light from the measurement environment can be reduced significantly.

Besides, because the luminometer apparatus of the present embodiment is equipped with the shutter 1011 configured to be openable and closable under the rotary plate 1005, it is possible to discard a reaction container 104 for which luminescence measurement is terminated downward from the rotary plate 1005, while the insertion opening 1008 remains closed. Consequently, it is possible to reduce the number of times the insertion opening 1008 is opened and closed and time during which it opens for discarding a reaction container 104, incursion of light from the measurement environment is reduced, and contamination from a worker is prevented.

Besides, for the luminometer apparatus of the present embodiment, at least one selected from a group consisting of an ATP extraction reagent, an ATP erasure reagent, and a reagent which increases ATP included within a cell is put into the holding containers 101 which are in turn loaded in the container rack 1003. Then, after the container rack 1003 is installed inside the light-shielded room 1006 and the insertion opening 1008 is closed, it is possible to perform a plurality of pretreatment operations inside the light-shielded room 1006 without intervention of a worker's hand, while maintaining the light-shielded environment and clean space. Consequently, while pretreatment is performed, incursion of light from the measurement environment is reduced and contamination from a worker is prevented.

Besides, according to the luminometer apparatus of the present embodiment, because the apparatus includes the thermostatic unit 9001 or the thermostatic unit 11001, it is possible to perform a plurality of pretreatment operations inside the light-shielded room 1003 without intervention of a worker's hand, while maintaining the light-shielded environment and clean space. Consequently, while pretreatment is performed, incursion of light from the measurement environment is reduced and contamination from a worker is prevented.

First Embodiment

Figure 8:
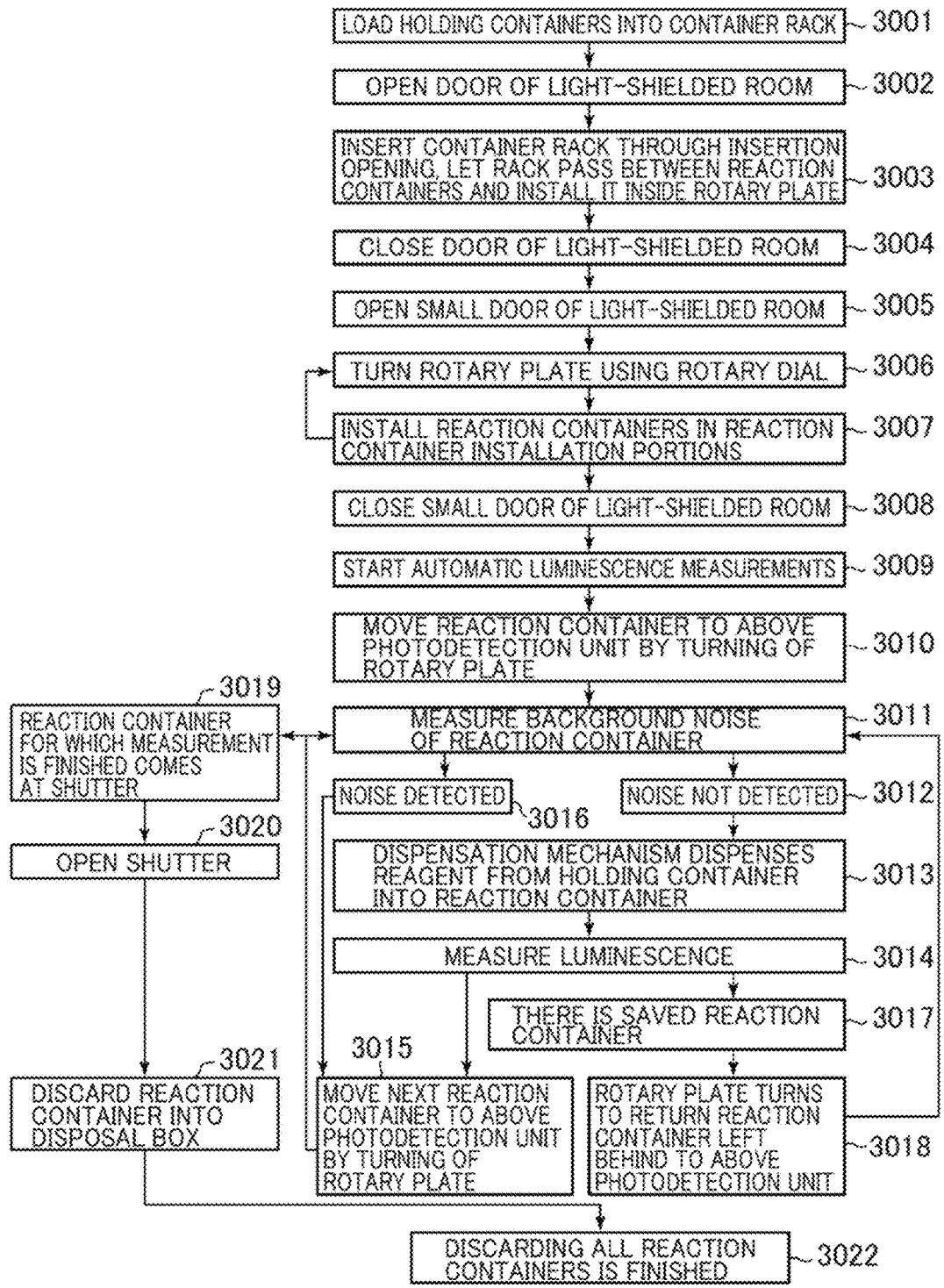
FIG. 8 is a stepwise diagram for explaining usage pertaining to a first embodiment of the luminometer apparatus.

A luminescence measurement method pertaining to a first embodiment, using the luminometer apparatus depicted in FIGS. 1 to 5, is described below according to FIG. 8.

The first embodiment is an embodiment in which, first, either one of a sample and a reagent is put into holding containers 101 which are loaded in the container rack 1003 and the other of them is put into reaction containers 104 which are held on the rotary plate 1005 and, after that, reagents or samples in the holding containers 101 are dispensed into the reaction containers 104.

That is, the first embodiment is an embodiment which includes installing the holding containers 101, each having a reagent put therein, on the container rack 1003, installing the reaction containers 104, each having a sample put therein, on the rotary plate 1005, and, after closing the insertion opening 1008, dispensing the reagents in the holding containers 101 into the reaction containers 104 or an embodiment which includes installing the holding containers 101, each having a sample put therein, on the container rack 1003, installing the reaction containers 104, each having a reagent put therein, on the rotary plate 1005, and, after closing the insertion opening 1008, dispensing samples in the holding containers 101 into the reaction containers 104.

A worker first sets reagents and samples in the light-shielded room 1006 according to a procedure as described below. First, put a reagent or sample into each of the holding containers 101 and load the holding containers 101 into the container rack 1003 (step 3001).

Figure 4:
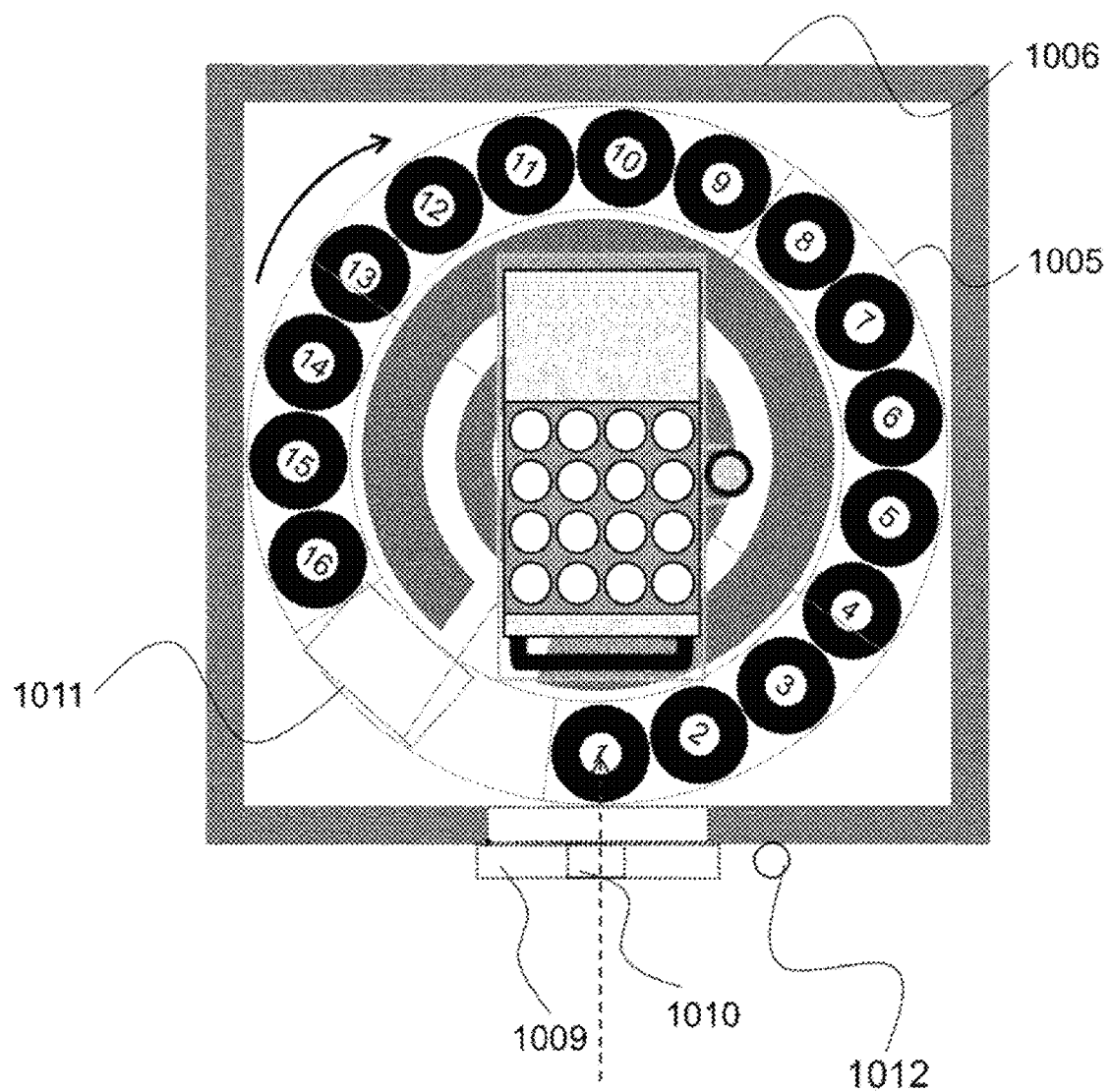
FIG. 4 is a diagram depicting the luminometer apparatus in a state when reaction containers are installed inside the light-shielded room.

Then, install the container rack 1003 inside the light-shielded room 1006, as depicted in FIG. 4. First, open the door 1009 of the light-shielded room. 1006 (step 3002). Move the slides 4001 on the rails 4002, pull out them from the insertion opening 1008, and mount the container rack 1003 on the slides 4001. Push the slides 4001 with the container rack 1003 mounted thereon toward the insertion opening 1008, let the container rack 1003 move on the rails 4002 to pass through the insertion opening 1008 and pass a space between reaction containers 104 having the gap 1007 therebetween, and install the container rack 1003 inside a region of passage of reaction containers 104, when turning (step 3003). Close the door 1009 (step 3004).

Then, install reaction containers 104 inside the light-shielded room 1006.

First, put a reagent or sample into each of the reaction containers 104. In the present embodiment, if a reagent is put in the holding containers 101, a sample should be put in the reaction containers 104; if a sample is put in the holding containers 101, a reagent should be put in the reaction containers 104. Descriptions are provided below for an instance in which a luminescent reagent, as a reagent, is put in the holding containers 101 and a sample is put in the reaction containers 104.

Next, open the small door 1010 of the light-shielded room 1006 (step 3005), as depicted in FIG. 4. Turn the rotary plate 1005 using the rotary dial 1012 (step 3006). Install a reaction container 104 No. 1 having a sample put therein in a reaction container installation portion 1004 No. 1 (step 3007). Turn the rotary plate 105 again, using the rotary dial 1012, and install a reaction container 104 No. 2 in a reaction container installation portion 1004 No. 2. Repeat this as many times as the number of reaction containers 104. After that, close the small door 1010 (step 3008).

Then, the worker gets luminescence measurements started and subsequent steps (3010) to (3022) are automatically executed by the control unit 2020 (step 3009).

The rotary plate 1005 turns to position a reaction container 104 No. 1 just above the photodetection unit 2003 (step 3010). The photodetection unit 2003 measures a background noise of the reaction container 104 No. 1 (step 3011).

[When a Background Noise is not Detected]

Figure 9:
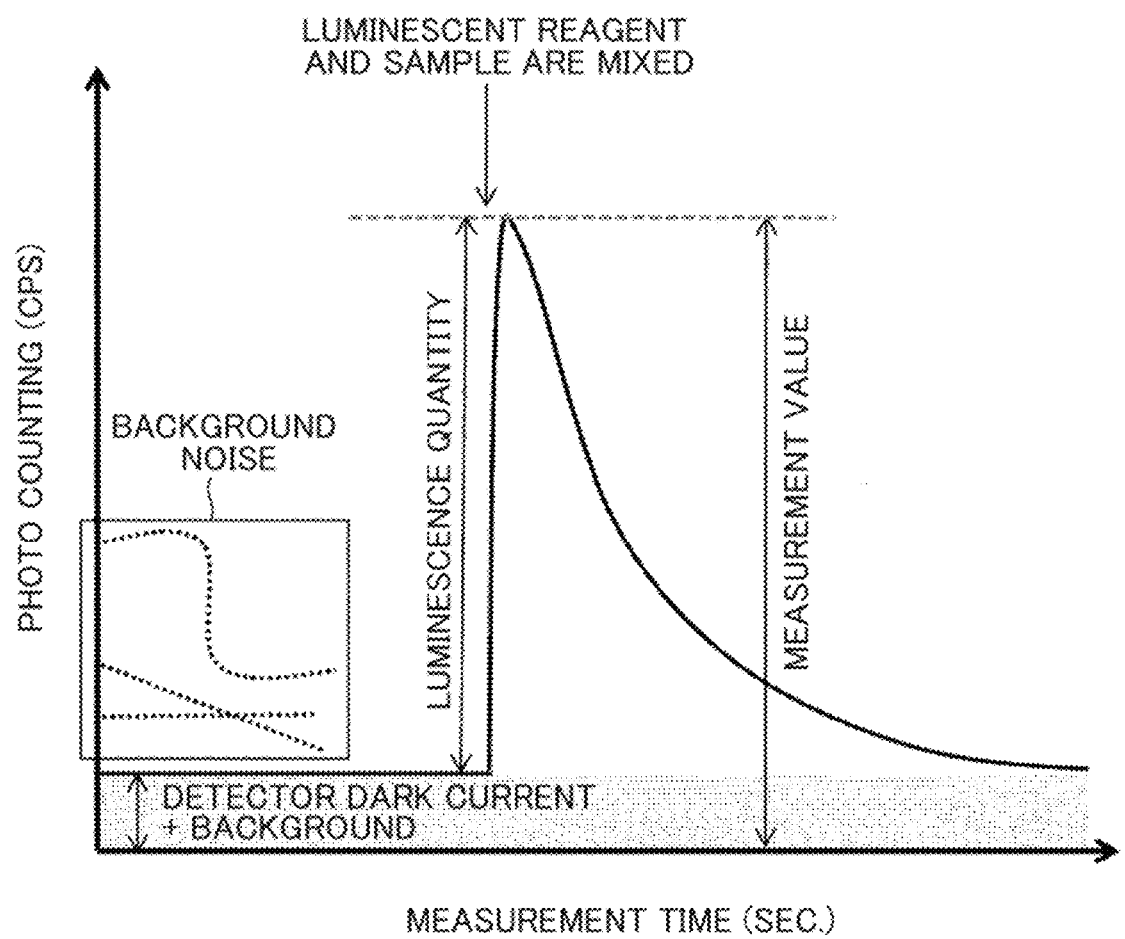
FIG. 9 is a diagram representing photo counting measurements obtained by a photodetection unit and changing with measurement time.

FIG. 9 represents photo counting measurements obtained by the photodetection unit 2003 and changing with measurement time.

When a background noise has not been detected from the start of measurement by the photodetection unit 2003 until a luminescent reagent and a sample are mixed, as illustrated in an example indicated by a solid line, a total value of detector dark current and background in the detection unit shows a constant value at a low level. When a background noise is not detected, the reaction container 104 No. 1 stays in the position where it is placed (step 3012).

Under control of the control unit 2020, the dispensation mechanism 2001 takes up a luminescent reagent in a holding container 101 on the container rack 1003 and pours the reagent into the reaction container 104 No. 1 (step 3013).

Luminescence generated by mixing of the luminescent reagent with a sample in the reaction container 104 is measured by the photodetection unit 2003 (step 3014). Upon completion of luminescence measurement, the rotary plate 1005 turns to position a reaction container 104 No. 2 just above the photodetection unit 2003 (step 3015). A background noise is measured again. This is repeated up to No. 16.

[When a Background Noise has been Detected]

Meanwhile, when a background noise has been detected from the start of measurement by the photodetection unit 2003 until a luminescent reagent and a sample are mixed, a total value of detector dark current and background varies, i.e., becomes constant at a high level or falls, as illustrated in an example indicated by a plurality of dashed lines in FIG. 9.

When the noise has been detected (step 3016), the rotary plate 1005 turns to position a reaction container 104 No. 2 just above the photodetection unit 2003 (step 3015), and the reaction container 104 No. 2 is saved. The photodetection unit 2003 measures a background noise of the reaction container 104 No. 2 (step 3011). When the noise has not been detected (step 3012), the dispensation mechanism 2001 under control of the control unit 2020 takes up a luminescent reagent in a holding container 101 on the container rack 1003 and pours the reagent into the reaction container 104 No. 2 (step 3013). Luminescence generated by mixing of the luminescent reagent with a sample in the reaction container 104 is measured by the photodetection unit 2003 (step 3014). Upon completion of luminescence measurement, because there is the saved reaction container 104 No. 1 for which measurement is unfinished (step 3017), the rotary plate 1005 turns to return and position the saved reaction container 104 No. 1 just above the photodetection unit 2003 (step 3018). A background noise is measured again (step 3011). This is repeated up to a reaction container 104 No. 16.

Figure 5:
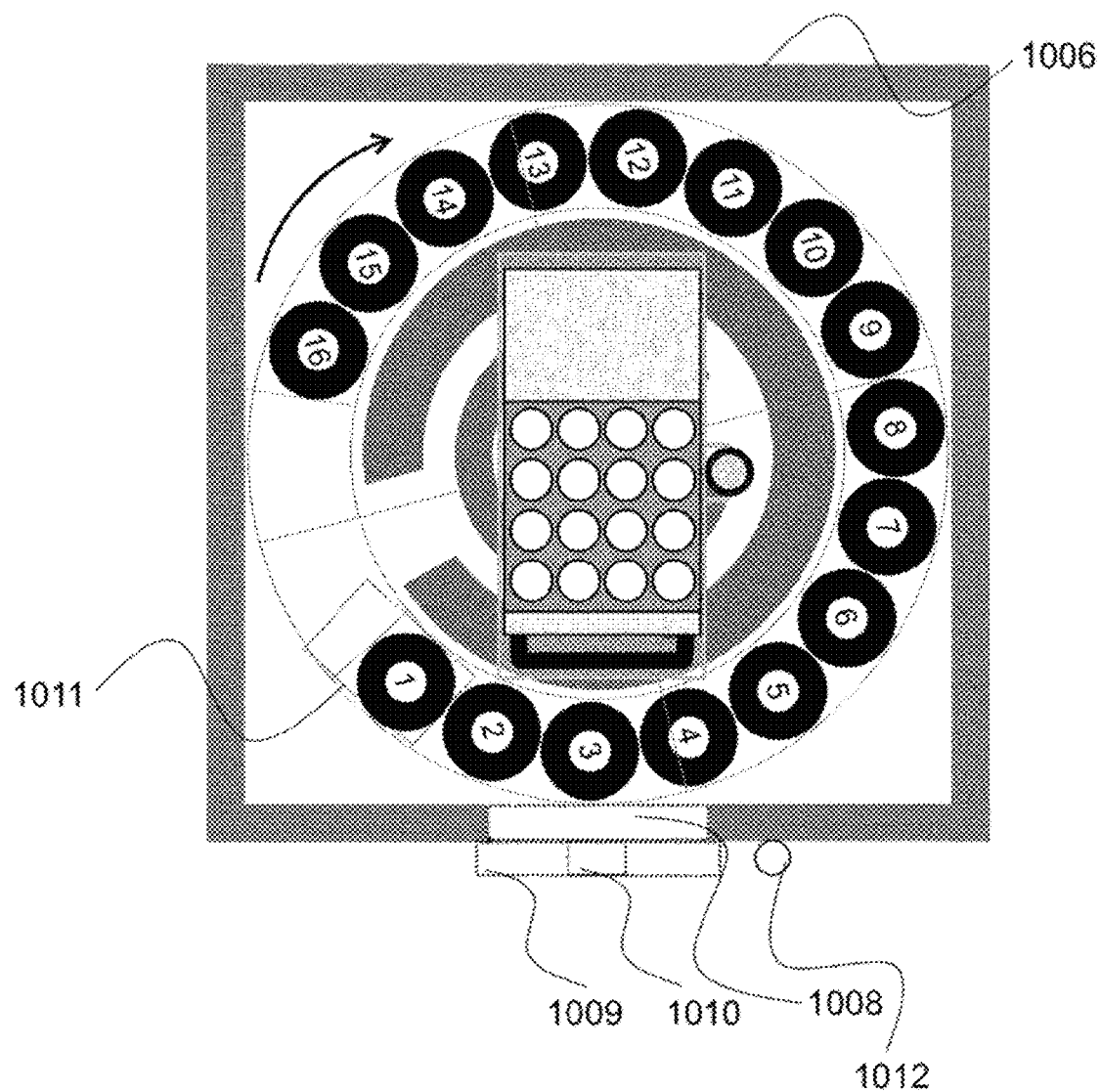
FIG. 5 is a diagram depicting the luminometer apparatus in a state in which a reaction container inside the light-shielded room is discarded from a shutter.

Then, a reaction container for which measurement is finished is discarded (see FIG. 5).

When each of the reaction containers 104 No. 1 and subsequent for which measurement is finished has come at the shutter 1011 (step 3019), the shutter 1011 opens (step 3020) and the reaction container 104 No. 11 is discarded into the disposal box 2012 (step 3021).

When luminescence measurements for all the reaction containers 104 (No. 1 to No. 16) and discarding them are finished, all the steps finish (step 3022).

Second Embodiment

Figure 10:
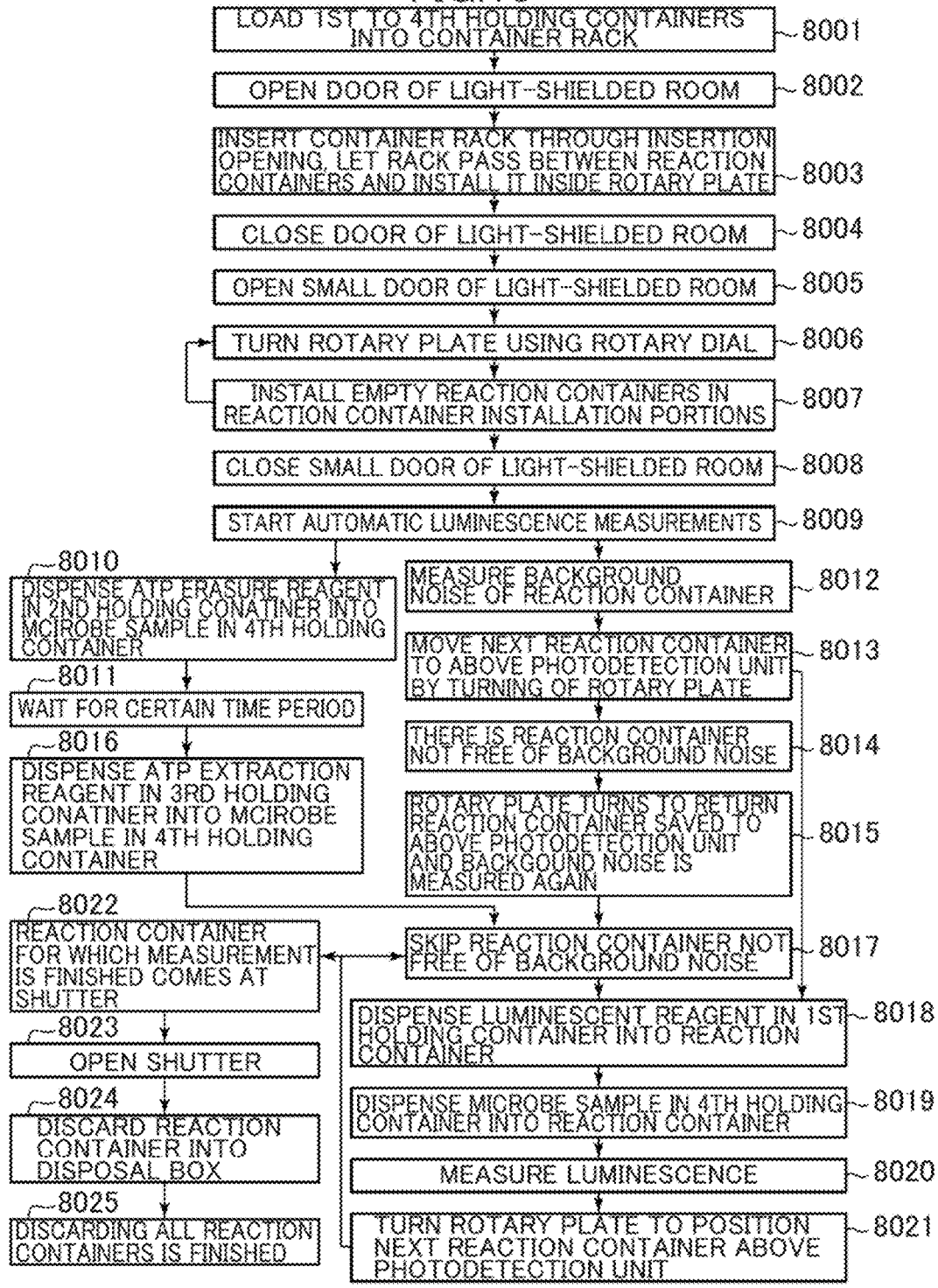
FIG. 10 is a stepwise diagram for explaining usage pertaining to a second embodiment of the luminometer apparatus.

A luminescence measurement method pertaining to a second embodiment, using the luminometer apparatus depicted in FIGS. 1 to 6, is described below according to FIG. 10.

The second embodiment is an embodiment which includes putting reagents and a sample discretely into holding containers 101, loading the holding containers into the container rack 1003, and installing reaction containers 104 which remain empty on the rotary plate 1005.

In the second embodiment, as a pretreatment, a reagent other than a luminescent reagent is mixed with a sample in the container rack 1003 and, concurrently with this pretreatment, a background of reaction containers 104 is checked.

That is, the second embodiment is an embodiment which includes the following: loading a first holding container 101a having a luminescent reagent put therein, a second holding container 101b having an ATP erasure reagent put therein, a third holding container 101c having an ATP extraction reagent put therein, and a fourth holding container 101d having a microbe sample put therein into the container rack 1003 (see FIG. 6); installing empty reaction containers 104 on the rotary plate 1005; after closing the insertion opening 1008, as a pretreatment, mixing the ATP erasure reagent in the second holding container 101b and the ATP extraction reagent in the third holding container 101c with the microbe sample in the fourth holding container 101d in the container rack 1003; concurrently with this pretreatment, performing a background check of the reaction containers 104; and, after that, dispensing mixture liquids prepared by the pretreatment into the empty reaction containers 104.

In the present embodiment, it is enabled to perform detecting a background noise of reaction containers 104 concurrently with sample pretreatment in the container rack 1003 and, therefore, luminescence measurements can be performed efficiently.

The present embodiment is easy to utilize when microbe samples need to be replaced at a high frequency in order to evaluate a change over time in drug sensitivity of a few microbes for various drugs coexisting with the microbes. It is also easy to utilize when handling samples of many kinds of microbes.

A worker first sets reagents and samples in the light-shielded room 1006 according to a procedure as described below.

First, put a luminescent reagent into the first holding container 101a, put an ATP erasure reagent into the second holding container 101b, put an ATP extraction reagent into the third holding container 101c, and put a sample of one of various microbes into the fourth holding container 101d, and load these first to fourth holding containers 101a to 101d into the container rack 1003 (step 8001).

Figure 3:
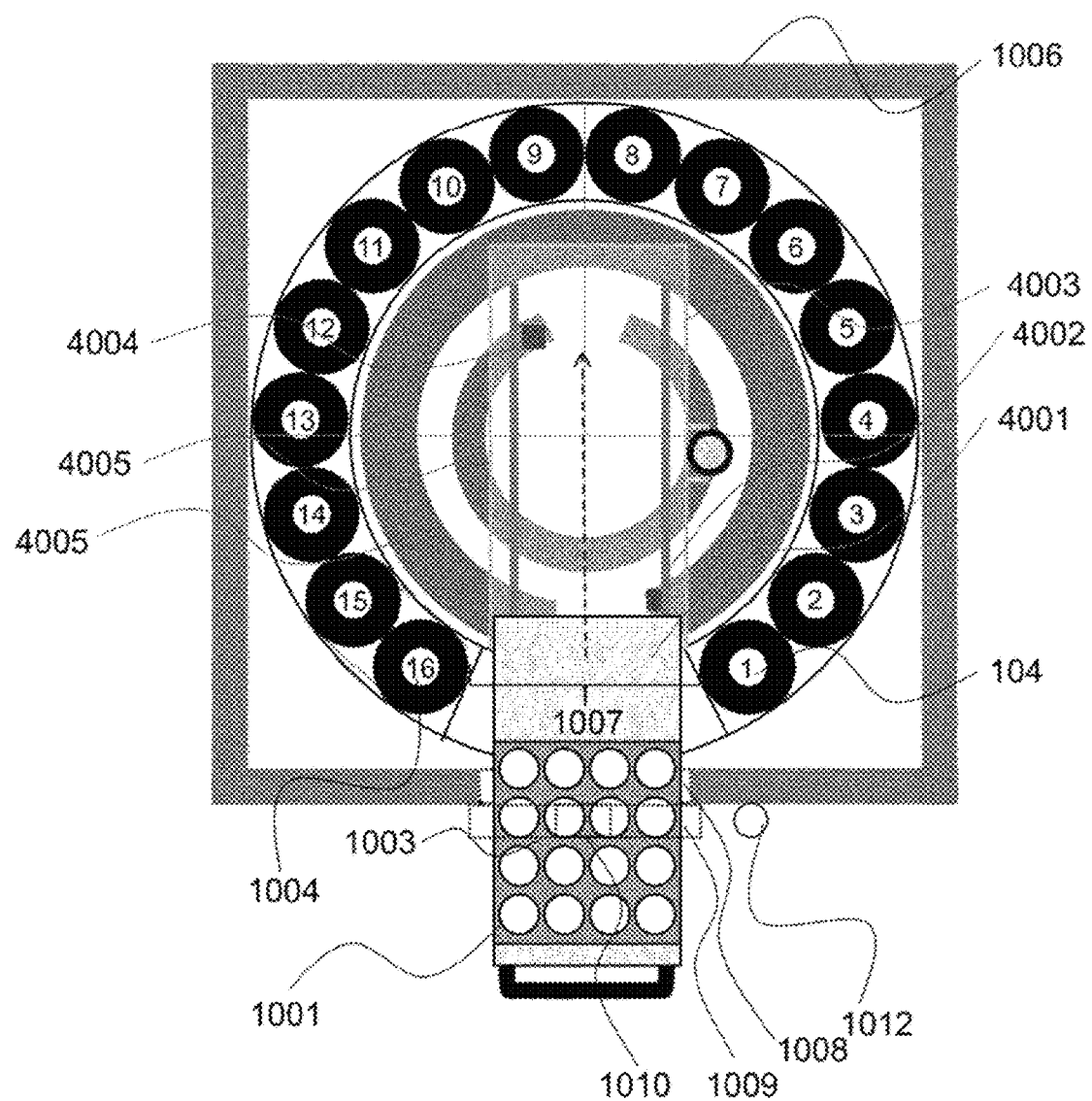
FIG. 3 is a diagram depicting the luminometer apparatus in a state when a container rack is inserted into a light-shielded room.

Then, install the container rack 1003 inside the light-shielded room 1006. As depicted in FIG. 3, first, open the door 1009 of the light-shielded room 1006 (step 8002).

As is the case for the first embodiment, pull out the container rack 1003 from the insertion opening 1008 and mount the container rack 1003 on the slides 4001. Push the slides 4001 with the container rack 1003 mounted thereon toward the insertion opening 1008, let the container rack 1003 move on the rails 4001 to pass through the insertion opening 1008 and pass a space between reaction containers 104 having the gap 1007 therebetween (between a reaction container 104 No. 1 and a reaction container 104 No. 16), and install the container rack 1003 inside a region of passage of reaction containers 104, when turning (step 8003). Close the door 1009 (step 8004).

Then, install reaction containers 104 inside the light-shielded room 1006. First, open the small door 1010 of the light-shielded room 1006 (step 8005), as depicted in FIG. 4. Turn the rotary plate 1005 using the rotary dial 1012 (step 8006). Install a reaction container 104 No. 1 which is empty in a reaction container installation portion 1004 No. 1 (step 8007). Turn the rotary plate 105 again, using the rotary dial 1012, and install a reaction container 104 No. 2 which is empty in a reaction container installation portion 1004 No. 2. Repeat this as many times as the number of reaction containers 104. After that, close the small door 1010 (step 8008).

Then, the worker gets luminescence measurements started and subsequent steps (8010) to (8025) are automatically executed by the control unit 2020 (step 8009).

Under control of the control unit 2020, the dispensation mechanism 2001 takes up an ATP erasure reagent in the second holding container 101b on the container rack 1003 and pours the reagent into a microbe sample in the fourth holding container 101d (step 8010).

At this point of time, all or a part of the container rack 1003 is maintained in a constant temperature condition (e.g., at 37° C.) for a certain time period (e.g., for 30 minutes) by the thermostatic unit 9001, as depicted in FIG. 6, thus erasing ATP other than ATP derived from a microbe in the microbe sample (step 8011).

Concurrently with dispensation and maintaining the container rack at constant temperature in (step 8010) and (step 8011), the rotary plate 1005 turns to position a reaction container 104 No. 1 just above the photodetection unit 2003 and the photodetection unit 2003 measures a background noise of the reaction container 104 No. 1 (step 8012).

Judgment as to whether or not a background noise is detected is made based on a photo counting measurement result, as illustrated in FIG. 9, in the same way as described for the first embodiment. After measuring a background noise of the reaction container 104 No. 1 finishes, the rotary plate 1005 turns to position a reaction container 104 No. 2 just above the photodetection unit 2003 (step 8013). A background noise is measured again. This is repeated up to a reaction container 104 No. 16.

When there is a reaction container 104 for which a background noise has been detected (step 804), the rotary plate 1005 turns to return and position the reaction container 104 for which a background noise has been detected just above the photodetection unit 2003 again and a background noise is measured again (step 8015).

Meanwhile, upon termination of maintaining the holding container 101 (a mixture liquid of the ATP erasure reagent and the microbe sample) at constant temperature by the thermostatic unit 9001, the dispensation mechanism 2001 under control of the control unit 2020 takes up an ATP extraction reagent in the third holding container 101c on the container rack 1003 and pours the reagent into a microbe sample in the fourth holding container 101d to extract ATP (step 8016).

Upon termination of ATP extraction, No. of a reaction container that is not free of a background noise is stored in a storage area and setting is performed to skip dispensation into that reaction container (step 8017).

Meanwhile, when there is not a reaction container 104 for which a background noise has been detected, the above (step 8015) and (step 8017) are skipped and the process goes to a next step upon termination of ATP extraction (step 8016).

The dispensation mechanism 2001 under control of the control unit 2020 takes up a luminescent reagent in the first holding container 101a on the container rack 1003 and pours the reagent into the reaction container 104 No. 1 (step 8018).

The dispensation mechanism 2001 under control of the control unit 2020 takes up a microbe sample in the fourth holding container 101d on the container rack 1003 and pours the sample into the reaction container 104 No. 1 having the luminescent reagent put therein (step 8019).

Luminescence generated by mixing of the luminescent reagent with the sample is measured by the photodetection unit 2003 (step 8020). Upon completion of luminescence measurement, the rotary plate 1005 turns to position a reaction container 104 No. 2 just above the photodetection unit 2003 (step 8021).

Dispensing the luminescent reagent (step 8018) and dispensing the microbe sample (step 8019) into reaction containers 104 other than a reaction container whose No. has been stored in the storage area and luminescence measurement (step 8020) are repeated up to No. 16.

Then, a reaction container 104 for which measurement is finished is discarded. As depicted in FIG. 5, as the rotary plate 1005 repeats turning, when each of the reaction containers 104 No. 1 and subsequent for which measurement is finished has come at the shutter 1011 (step 8022), the shutter 1011 opens (step 8023) and the reaction container 104 is discarded into the disposal box 2012 (step 8024).

When luminescence measurements for all the reaction containers 104 No. 1 to No. 16 and discarding them are finished, all the steps finish (step 8025).

Third Embodiment

Figure 11:
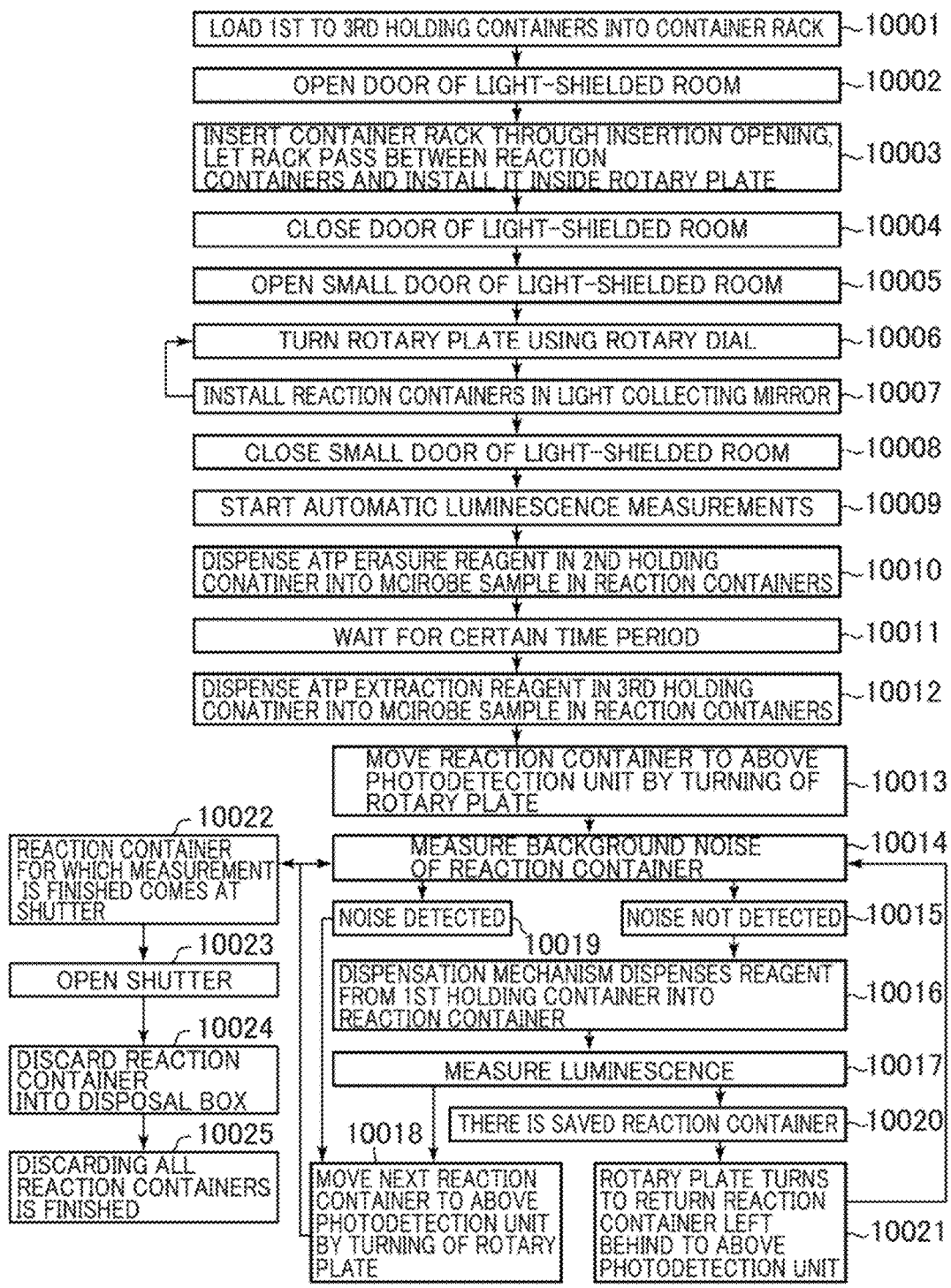
FIG. 11 is a stepwise diagram for explaining usage pertaining to a third embodiment of the luminometer apparatus.

A luminescence measurement method pertaining to a third embodiment, using the luminometer apparatus depicted in FIGS. 1 to 5 and FIG. 7, is described below according to FIG. 11.

The third embodiment is an embodiment which includes putting various reagents discretely into holding containers 101, loading the holding containers into the container rack 1003, putting a microbe sample into reaction containers 104, and installing the reaction containers on the rotary table 1005.

The third embodiment is an embodiment in which the dispensation mechanism 2001 dispenses only reagents, but does not need to dispense a microbe sample. This embodiment also enables a treatment of maintaining a microbe sample at constant temperature on the rotary plate 1005.

That is, the third embodiment is an embodiment which includes the following: loading a first holding container 101a having a luminescent reagent put therein, a second holding container 101b having an ATP erasure reagent put therein, and a third holding container 101c having an ATP extraction reagent put therein into the container rack 1003; installing reaction containers 104 having a microbe sample put therein on the rotary plate 1005; after closing the insertion opening 1008, dispensing reagents in the first to third holding containers 101a to 101c into the reaction containers 104 having the microbe sample put therein.

According to the third embodiment, because background measurements of reaction containers 104 with a sample being put therein can be performed, a luminescent phenomenon of a sample by itself before being mixed with a luminescent reagent can also be observed, besides such phenomenon attributed to reaction containers 104. Also, in the third embodiment, reagents only need to be set on the container rack 1003 and, therefore, preparation of the container rack 1003 can be performed simply.

A worker first sets reagents and samples in the light-shielded room 1006 according to a procedure as described below.

First, put a luminescent reagent into the first holding container 101a, put an ATP erasure reagent into the second holding container 101b, put an ATP extraction reagent into the third holding container 101c, and load the first to third holding containers 101a to 101c into the container rack 1003 (step 10001).

Then, install the container rack 1003 inside the light-shielded room 1006. As depicted in FIG. 3, first, open the door 1009 of the light-shielded room 1006 (step 10002).

As is the case for the first embodiment, pull out the container rack 1003 from the insertion opening 1008 and mount the container rack 1003 on the slides 4001. Push the slides 4001 with the container rack 1003 mounted thereon toward the insertion opening 1008, let the container rack 1003 move on the rails 4002 to pass through the insertion opening 1008 and pass a space between reaction containers 104 having the gap 1007 therebetween (between a reaction container 104 No. 1 and a reaction container 104 No. 16), and install the container rack 1003 inside a region of passage of reaction containers 104, when turning (step 10003). Close the door 1009 (step 10004).

Then, install reaction containers 104 inside the light-shielded room 1006. First, put a sample into the reaction containers 104. Then, open the small door 1010 of the light-shielded room 1006 (step 10005), as depicted in FIG. 4. Turn the rotary plate 1005 using the rotary dial 1012 (step 10006).

Install a reaction container 104 No. 1 with a microbe sample put therein in a reaction container installation portion 1004 No. 1 (step 10007). Turn the rotary plate 105 again, using the rotary dial 1012, and install a reaction container 104 No. 2 with a microbe sample put therein in a reaction container installation portion 1004 No. 2. Repeat this as many times as the number of reaction containers 104. After that, close the small door 1010 (step 10008).

Then, the worker gets luminescence measurements started and subsequent steps (10010) to (10025) are automatically executed by the control unit 2020 (step 10009).

Under control of the control unit 2020, the dispensation mechanism 2001 takes up an ATP erasure reagent in the second holding container 101b on the container rack 1003 and pours the reagent into a microbe sample in the reaction containers 104 (step 10010).

The reaction containers 104 are maintained in a constant temperature condition (e.g., at 37° C.) for a certain time period (e.g., for 30 minutes) by the thermostatic unit 11001, as depicted in FIG. 7, thus erasing ATP other than ATP derived from a microbe in the microbe sample (step 10011).

Upon termination of the constant temperature treatment, the dispensation mechanism 2001 under control of the control unit 2020 takes up an ATP extraction reagent in the third holding container 101c on the container rack 1003 and pours the reagent into a microbe sample in the reaction containers 104 (step 10012).

As depicted in FIG. 1, the rotary plate 1005 turns to position a reaction container 104 No. 1 just above the photodetection unit 2003 (step 10013). The photodetection unit 2003 measures a background noise of the reaction container 104 No. 1 (step 10014).

[When a Background Noise is not Detected]

Judgment as to whether or not a background noise is detected is made based on a photo counting measurement result, as illustrated in FIG. 9, in the same way as described for the first embodiment.

When a background noise is not detected, as illustrated in FIG. 9, the reaction container 104 No. 1 stays in the position where it is placed (step 10015).

Under control of the control unit 2020, the dispensation mechanism 2001 takes up a luminescent reagent in the first holding container 101*a* on the container rack 1003 and pours the reagent into the reaction containers 104 No. 1 (step 10016).

Luminescence generated by mixing of the luminescent reagent with a sample in the reaction container 104 is measured by the photodetection unit 2003 (step 10017). Upon completion of luminescence measurement, the rotary plate 1005 turns to position a reaction container 104 No. 2 just above the photodetection unit 2003 (step 10018). A background noise is measured again. This is repeated up to No. 16.

[When a Background Noise has been Detected]

When the noise has been detected (step 10019), as illustrated in FIG. 9, the rotary plate 1005 turns to position a reaction container 104 No. 2 just above the photodetection unit 2003 (step 10018), and the reaction container 104 No. 1 is saved. The photodetection unit 2003 measures a background noise of the reaction container 104 No. 2 (step 10014).

When the noise of the reaction container 104 No. 2 has not been detected (step 10015), the dispensation mechanism 2001 under control of the control unit 2020 takes up a luminescent reagent in the first holding container 101*a* on the container rack 1003 and pours the reagent into the reaction containers 104 No. 2 (step 10016).

Luminescence generated by mixing of the luminescent reagent with a sample in the reaction container 104 is measured by the photodetection unit 2003 (step 10017). Upon completion of luminescence measurement, because there is the saved reaction container 104 No. 1 for which measurement is unfinished (step 10020), the rotary plate 1005 turns to return and position the saved reaction container 104 No. 1 just above the photodetection unit 2003 (step 10021). A background noise is measured again (step 10014). This is repeated up to a reaction container 104 No. 16.

Then, a reaction container for which measurement is finished is discarded. As depicted in FIG. 5, when each of the reaction containers 104 No. 1 and subsequent for which measurement is finished has come at the shutter 1011 (step 10022), the shutter 1011 opens (step 10023) and the reaction container 104 No. 1 is discarded into the disposal box 2012 (step 10024).

When luminescence measurements for all the reaction containers 104 No. 1 to No. 16 and discarding them are finished, all the steps finish (step 10025).

The first to third embodiments have been described hereinbefore, taking as an example of the case where the ATP luminometric assay was applied to the luminometer apparatus depicted in FIGS. 1 to 7; however, usage of the luminometer apparatus depicted in FIGS. 1 to 7 is not necessarily limited to the application to luminescence measurements by the ATP luminometric assay.

First to Third Embodiments

Figure 12:
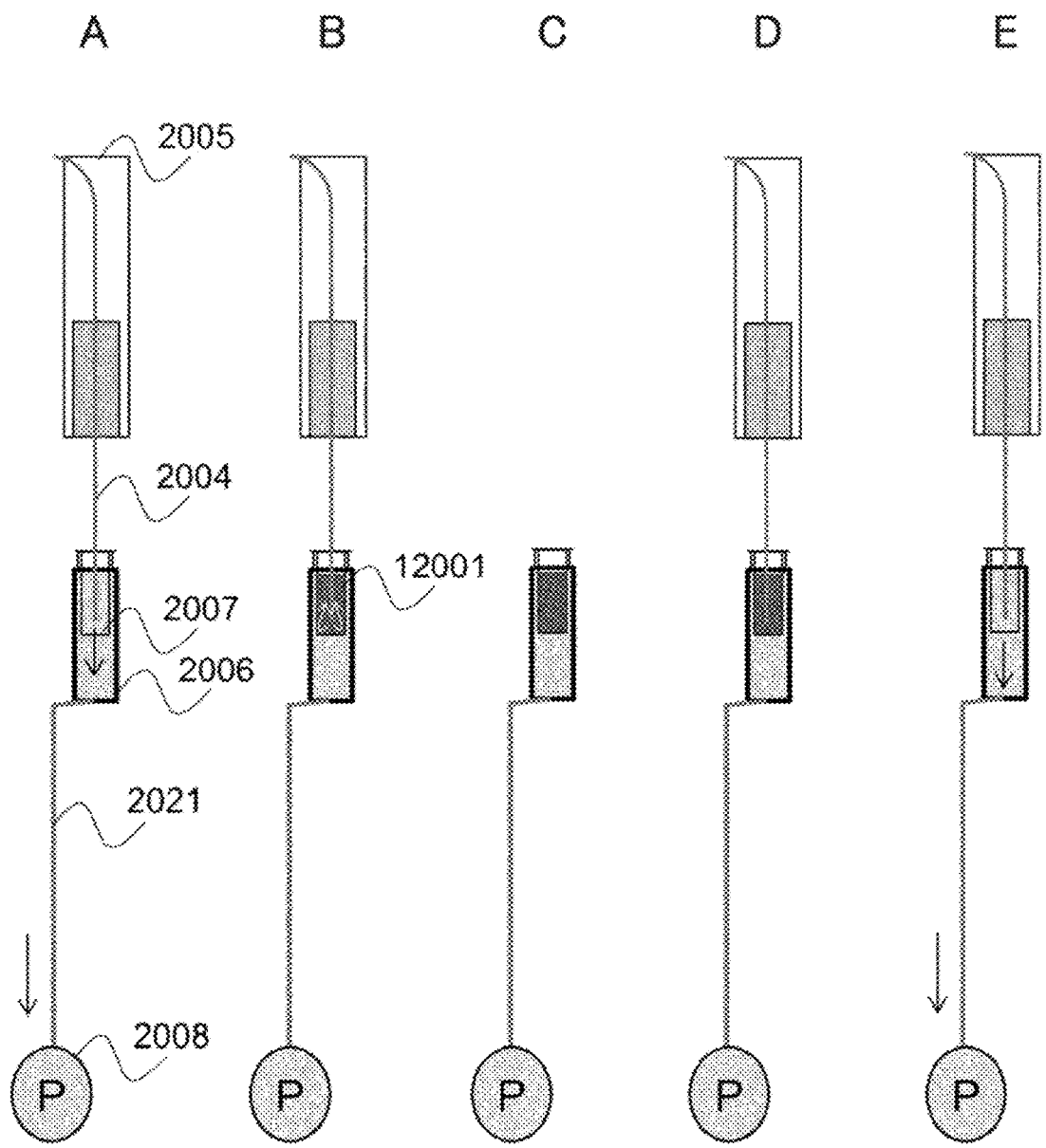
FIG. 12 is a diagram for explaining the actions of a nozzle and a suction unit, when the nozzle is cleaned.

Then, a nozzle cleaning process is described. FIG. 12 is a diagram for explaining the actions of the nozzle and the suction unit when the nozzle is cleaned.

Before taking up at least any one of reagents and samples in holding containers 101, the nozzle 2004 is guided to set over the filter 2007 within the cylindrical body 2006 by the arm 2005 driven by the control unit 2020.

Then, the control unit 2020 gets the suction action of the suction unit 2008 started. Concurrently with the suction by the suction unit 2008, a cleaning solution sucked into the nozzle 2004 is pushed out by the syringe 2010 via the three-way valve 2009 and ejected onto the filter 2007 within the cylindrical body 2006. Thereby, the inner surface of the nozzle 2004 is cleaned. The cleaning solution on the filter 2007 is ejected soon out of the cylindrical body 2006 by suction by the suction unit 2008 (FIG. 12A).

In turn, the control unit 2020 deactivates the suction unit 2008. By pushing out action of the syringe 2010, again, the cleaning solution sucked into the nozzle 2004 is expelled onto the filter 2007 within the cylindrical body 2006. Because the suction unit 2008 is inactive, the cleaning solution 12001 expelled onto the filter 2007 accumulates in the filter 2007. By immersing the tip of the nozzle 2004 in this cleaning solution 12001, the outer surface of the nozzle 2004 is cleaned (FIG. 12B).

Subsequently, even when the nozzle 2004 takes up at least any one of reagents and samples in holding containers 101, the suction unit 2008 is inactive successively and, therefore, the cleaning solution 12001 continues to accumulate in the filter 2007 by resistance of the filter 2007 (FIG. 12C).

In turn, after the control unit 2020 drives the arm 2005 and the nozzle 2004 takes up at least any one of reagents and samples in holding containers 101 and pours the taken up reagent or sample into a reaction container 104, the nozzle 2004 is moved to be set over the cylindrical body 2006 again and its tip is immersed into the cleaning solution 12001. Thereby, the outer surface of the nozzle 2004 onto which at least either a reagent or a sample has been deposited is cleaned (FIG. 12D).

After cleaning the outer surface of the nozzle 2004, the control unit 2020 gets the suction action of the suction unit 2008 started to eject the cleaning solution in the filter 2007 (FIG. 12E). The nozzle 20004 dispenses at least any one of reagents and samples taken up by it and cleaning the inner surface of the nozzle 2004 (FIG. 12A) is started again.

In this way, it is enabled to clean the inner and outer surfaces of the dispensation mechanism 2001 without intervention of a practical operation by a worker, while maintaining the light-shielded environment and clean space. Also, the cleaning can be performed, keeping the amount of using the cleaning solution as small as possible and consumable members for cleaning are not necessary.

According to the luminometer apparatus pertaining to the embodiments described hereinbefore, dispensing a reagent or sample in a holding container 101 into reaction containers 104, turning of the rotary plate 1005, and discarding the reaction containers 104 can be carried out without opening the insertion opening 1008, while the light-shielded room 1006 remains closed. Hence, it is possible to prevent luminescence derived from sample containers (background noise) and prevent contamination from a worker. It is thus possible to perform luminescence measurements of various kinds of microbes directly or included in a sample in a short time and at a high sensitivity; the microbes include living cells, dead cells, bacteria, true fungi (such as yeasts and molds), spores, sporules, and fungi such as nonsporulating, aerobic, anaerobic, gram-negative, or gram-positive ones.

Besides, according to the luminometer apparatus pertaining to the embodiments, the container rack 1003 loaded with samples or reagents is installed inside the rotary plate 1005 and a reaction container 104 not subjected to luminance measurement and a reaction container 104 for which luminance measurement is finished are automatically discarded into one place (the disposal box 2012). Hence, the apparatus as a whole is easy to downsize and light shielding management and cleanliness management are easy to perform. Therefore, it is possible to perform high-sensitivity luminescence measurements for which a background noise derived from sample containers can be prevented and no contamination occurs from the measurement environment or a worker; besides, power and space necessary for cleanliness management can be reduced. Hence, it is possible to minimize a risk of contamination.

Moreover, according to the luminometer apparatus pertaining to the embodiments described hereinbefore, even when luminescence derived from a sample container is detected at the step of luminescence detection by the photodetection unit 2003, the reaction container 104 with a sample being put therein can be saved temporarily under the light-shielded environment. At this time, because the reaction container 104 is preserved under the light-shielded environment, further incursion of light that makes the reaction container 104 luminescent is prevented and it can be rechecked to see if luminescence no longer occurs from the reaction container 104. Hence, as for such a reaction container 104 that has become non-luminescent, discarding (losing) the reaction container 104 and the sample and sample replacement are not necessary and it is possible to perform luminescence measurements of various kinds of microbes in a short time, at a high sensitivity, and in an efficient manner.

LIST OF REFERENCE SIGNS

101 . . . Holding container,
1001 . . . Holding container installation portion,
1003 . . . Container rack,
104 (No. 1 to No. 16) . . . Reaction container,
104 (No. 1 to No. 16) . . . Reaction container installation portion,
1005 . . . Rotary plate,
1006 . . . Light-shielded room,
1007 . . . Gap,
1008 . . . Insertion opening,
1009 . . . Door,
1010 . . . Small door,
1011 . . . Shutter,
1012 . . . Rotary dial,
1013 . . . Light collecting mirror,
1100 . . . Rotary plate supporting plate,
2001 . . . Dispensation mechanism,
2002 . . . Opening,
2003 . . . Photodetection unit,
2004 . . . Nozzle,
2005 . . . Arm,
2006 . . . Cylindrical body,
2007 . . . Filter,
2008 . . . Suction unit,
2009 . . . Three-way valve,
2010 . . . Syringe,
2011 . . . Cleaning solution tank,
2012 . . . reaction disposal box,
2013 . . . Photodetection unit protecting material,
2014 . . . Rotary plate turning unit,
2020 . . . Dispensation mechanism control unit,
2021 . . . Tube,
2022 . . . Partition wall,
2023 . . . Suction tube,
4001 . . . Slides,
4002 . . . Rails,
4003 . . . Supporting pedestal,
4004 . . . Strut,
4005 . . . Strut avoidance opening,
9001 . . . Thermostatic unit,
11001 . . . Thermostatic unit,
12001 . . . Cleaning solution

The invention claimed is:

1. A luminometer apparatus inside a light-shielded room shielded from external light, the luminometer apparatus comprising:
a container rack that is loaded with holding containers, each discretely accommodating at least one selected from a sample and a luminescent reagent which produces a luminescent reaction when mixed with the sample;
a rotary plate that turns, while holding a plurality of reaction containers which accommodate a mixture liquid of the sample and the luminescent reagent along an outer circumference of the rotary plate, wherein the rotary plate includes a centrally positioned support configured to support the container rack, wherein the rotary plate includes a gap formed between at least a pair of adjacent reaction containers of the plurality of reaction containers, and wherein the rotary plate is provided with a transporter configured to transport the container rack to the centrally positioned support through the gap;
a dispensation mechanism configured to dispense said sample or luminescent reagent into a reaction container of the plurality of reaction containers held by the rotary plate; and
a photodetector disposed below an opening of the rotary plate and facing a bottom surface of a reaction container of the plurality of the reaction containers held by the rotary plate, the photodetector is configured to perform luminescence measurements in a state where the light-shielded room is closed,
wherein the light-shielded room has an insertion opening having a width allowing for insertion of the container rack and configured to be openable and closable, and
the rotary plate configured to be turnable in a state where the light-shielded room is closed.

2. The luminometer apparatus according to claim 1, wherein the dispensation mechanism is provided so as to be capable of dispensing a liquid in a state where the light-shielded room is closed.

3. The luminometer apparatus according to claim 1, wherein the light-shielded room is provided with a door to open and close the insertion opening and the door is provided with a second door which is narrower than the door.

4. The luminometer apparatus according to claim 1, wherein a rotary dial to turn the rotary plate is provided on the outside of the light-shielded room.

5. The luminometer apparatus according to claim 1, wherein the rotary plate is provided with a shutter on its underside, the shutter being openable and closable in a state where the light-shielded room is closed.

6. The luminometer apparatus according to claim 5, wherein the luminometer apparatus is equipped with a control unit that controls the rotary plate, the dispensation mechanism, the photodetection unit, and the shutter individually.

7. The luminometer apparatus according to claim 1, wherein at least one selected from a group consisting of a reagent which decomposes a substance other than a cell included in the sample, a reagent which increases a substance within a cell included in the sample, and a reagent which decomposes a cell included in the sample is put into the holding containers.

8. The luminometer apparatus according to claim 1, wherein the luminometer apparatus is configured to heat at least one of the holding containers and the plurality of reaction containers and keep the at least one of the holding containers and the plurality of reaction containers in a constant temperature condition.

9. The luminometer apparatus according to claim 1, wherein the transporter comprises a supporting pedestal equipped with rails provided in a central region of the rotary plate, and the container rack is held on slides provided to be movable on the rails.

10. The luminometer apparatus according to claim 1, wherein the luminometer apparatus is provided with a suction unit that has a cylindrical body at its far end and sucks in a liquid fed into a space inside the cylindrical body, a bottomed filter is provided to fit in with the inner wall of the cylindrical body inside the cylindrical body.

11. The luminometer apparatus according to claim 10, wherein a cleaning solution tank holding a cleaning solution is connected to the dispensation mechanism.

12. The luminometer apparatus according to claim 11, wherein a control unit moves a tip of the dispensation mechanism to above the cylindrical body and controls the dispensation mechanism to eject a cleaning solution sucked in it from the cleaning solution tank into a space inside the filter when suction is performed by the suction unit and controls the dispensation mechanism to eject a cleaning solution sucked in it from the cleaning solution tank into a space inside the filter and immerse the tip of the dispensation mechanism into the cleaning solution accumulated in the filter when suction is not performed by the suction unit.

13. The luminometer apparatus according to claim 12, wherein before dispensation of the reagent or the sample put into the holding containers is dispensed into the plurality of reaction containers, the control unit moves the tip of the dispensation mechanism to above the cylindrical body and causes the dispensation mechanism to eject a cleaning solution sucked in it from the cleaning solution tank into a space inside the filter when suction is not performed by the suction unit, and after dispensation of the reagent or the sample put into the holding containers is dispensed into the plurality of reaction containers, the control unit moves again the tip of the dispensation mechanism to above the cylindrical body and controls the dispensation mechanism to immerse the tip of the dispensation mechanism into the cleaning solution accumulated in the filter.

* * * * *